United States Patent
DuBuffet et al.

(10) Patent No.: US 8,436,206 B2
(45) Date of Patent: May 7, 2013

(54) PROCESS FOR THE SYNTHESIS OF (7-METHOXY-1-NAPHTHYL) ACETONITRILE AND APPLICATION IN THE SYNTHESIS OF AGOMELATINE

(75) Inventors: Thierry DuBuffet, Autretot (FR); Jean-Pierre Lecouve, Le Havre (FR); Jean-Paul Hermet, Thonon-les-Bains (FR)

(73) Assignee: Les Laboratoires Servier, Suresnes Cedex (FR)

( * ) Notice: Subject to any disclaimer, the term of this patent is extended or adjusted under 35 U.S.C. 154(b) by 0 days.

(21) Appl. No.: 13/561,421

(22) Filed: Jul. 30, 2012

(65) Prior Publication Data

US 2012/0330062 A1    Dec. 27, 2012

Related U.S. Application Data

(62) Division of application No. 12/733,034, filed as application No. PCT/FR2008/001146 on Aug. 1, 2008, now Pat. No. 8,252,951.

(30) Foreign Application Priority Data

Aug. 3, 2007  (FR) ...................................... 07 05688

(51) Int. Cl.
   *C07C 231/02*    (2006.01)
(52) U.S. Cl.
   USPC ......................................................... 564/144

(58) Field of Classification Search ........................ None
See application file for complete search history.

(56) References Cited

FOREIGN PATENT DOCUMENTS

| EP | 0709371 | 5/1996 |
|----|---------|--------|
| EP | 1564202 | 8/2005 |

OTHER PUBLICATIONS

Arrowsmith. et al., "Physical properties amd chemical constitution. Part XLI. Naphthalene compounds"Journal of the Chemical Society, p. 2072-3078, 1965.
International Search Report for PCT/FR2008/001146 of Jun. 2, 2009.
Schreiber, et al., "Conjugationin the naphtalene series, II Solvolysis fo x-methoxy-y-bromomethylnaphthalenes" Journal of the American Chemical Society, vol. 84, p. 860, 1962.

*Primary Examiner* — Kamal Saeed
(74) *Attorney, Agent, or Firm* — Hueschen and Sage

(57) ABSTRACT

Process for the industrial synthesis of the compound of formula (I)

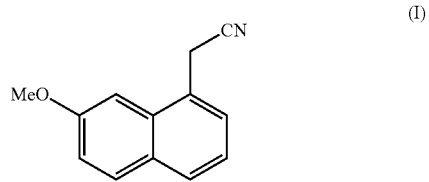

Application of such process in the synthesis of agomelatine.

4 Claims, No Drawings

PROCESS FOR THE SYNTHESIS OF (7-METHOXY-1-NAPHTHYL) ACETONITRILE AND APPLICATION IN THE SYNTHESIS OF AGOMELATINE

The present invention relates to a process for the industrial synthesis of (7-methoxy-1-naphthyl)acetonitrile and to its application in the industrial production of agomelatine, or N-[2-(7-methoxy-1-naphthyl)ethyl]acetamide.

More specifically, the present invention relates to a process for the industrial synthesis of the compound of formula (I):

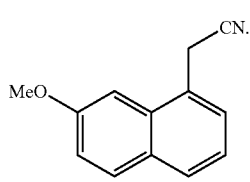

The compound of formula (I) obtained according to the process of the invention is useful in the synthesis of agomelatine, or N-[2-(7-methoxy-1-naphthyl)ethyl]acetamide, of formula (II):

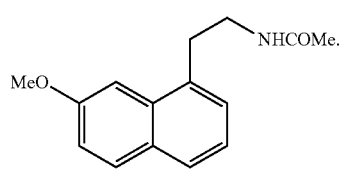

Agomelatine, or N-[2-(7-methoxy-1-naphthyl)ethyl]acetamide, has valuable pharmacological properties.

It has, in fact, the double characteristic of being, on the one hand, an agonist of receptors of the melatoninergic system and, on the other hand, an antagonist of the 5-HT$_{2C}$ receptor. These properties provide it with activity in the central nervous system and, more especially, in the treatment of major depression, seasonal affective disorder, sleep disorders, cardiovascular pathologies, pathologies of the digestive system, insomnia and fatigue due to jet-lag, appetite disorders and obesity.

Agomelatine, its preparation and its use in therapeutics have been described in European Patent EP 0 447 285, and also in European Patent Application EP 1 564 202.

In view of the pharmaceutical value of this compound, it is important to be able to obtain it by an effective industrial synthesis process that is readily transferable to an industrial scale and that results in agomelatine in a good yield and with excellent purity, starting from economical and readily obtainable starting materials.

Patent EP 0 447 285 describes the preparation, in eight steps, starting from 7-methoxy-1-tetralone, of agomelatine in an average yield of less than 30%. In particular, the preparation of (7-methoxy-1-naphthyl)acetonitrile involves six reaction steps, and difficulties in implementing that process rapidly came to light once it had been transferred to an industrial scale.

The literature describes obtaining (7-methoxy-1-naphthyl)acetonitrile in three steps starting from 7-methoxy-1-tetralone, by the action of LiCH$_2$CN followed by dehydrogenation with DDQ (2,3-dichloro-5,6-dicyano-1,4-benzoquinone) and finally by dehydration in an acid medium (Synthetic Communication, 2001, 31(4), 621-629). However, the overall yield is mediocre (76%) and, in particular, the DDQ used in the dehydrogenation reaction and also the benzene reflux necessary in the third step do not satisfy industrial requirements in terms of cost and the environment.

Patent Application EP 1,564,202 describes an especially advantageous industrial process which requires only four steps starting from 7-methoxy-1-tetralone, including two steps to obtain (7-methoxy-1-naphthyl)acetonitrile, having an average overall yield of more than 60%.

Although various synthesis procedures of the prior art describe the preparation of (7-methoxy-1-naphthyl)acetonitrile, most of them use 7-methoxy-1-tetralone as starting material, which is a costly compound whose synthesis is problematic. Accordingly, the development of new synthesis routes that are simple and reproducible and that utilise other starting materials still remains a necessity to this day.

The Applicant has now developed a new industrial synthesis which, in reproducible manner and without requiring laborious purification, yields agomelatine having a purity that is compatible with its use as a pharmaceutical active ingredient, starting from a less costly and more readily obtainable starting material.

In particular, the Applicant has now developed a new industrial synthesis process which makes it possible to obtain (7-methoxy-1-naphthyl)acetonitrile in reproducible manner and without requiring laborious purification, using 7-methoxy-1-naphthoic acid as starting material. The preparation of 7-methoxy-1-naphthoic acid is described in the prior art by D. Becker et al., starting from anisole, in excellent yields: Tetrahedron Letters, 27 (32), 3775-3776, 1986.

More specifically, the present invention relates to a process for the industrial synthesis of the compound of formula (I):

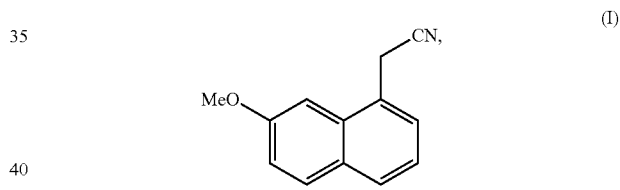

which process is characterised in that 7-methoxy-1-naphthoic acid of formula (III) is used for the reaction:

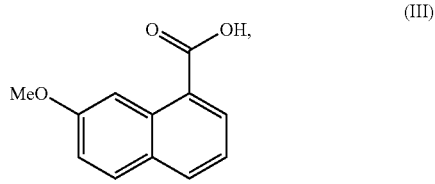 [SMILES: COc1ccc2cccc(C(=O)O)c2c1]

which is subjected to the action of a reducing agent to yield the compound of formula (IV):

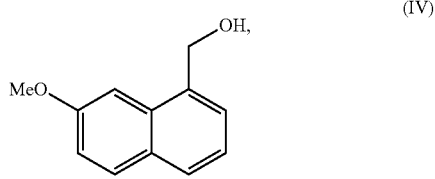

the OH function of which compound of formula (IV) is converted into a leaving group and which is reacted with a cyanation reagent to yield the compound of formula (I), which is isolated in the form of a solid.

Among the reducing agents that may be used for the reduction of the acid of formula (III) in the process of the present invention there may be mentioned, without implying any limitation, $BH_3$, $NaBH_4/AlCl_3$, 9-borabicyclo[3.3.1]nonane, $LiAlH_4$, $AlH_3$, diisobutylaluminium hydride (DIBAL-H) and, more especially, $BH_3$-THF.
The reduction of the acid of formula (III) in the process of the present invention may also be carried out, advantageously, after conversion of the acid of formula (III) into an acid derivative and, more particularly, into an ester, followed by reduction of that acid derivative into the alcohol of formula (IV), using the reducing agents $LiAlH_4$, $NaBH_4$ associated or not associated with MeOH, $LiBH_4$, DIBAL-H or bis(2-methoxyethoxy)-aluminium sodium hydride (Red-Al).

Advantageously, the OH group of the compound of formula (IV) of the process of the present invention is converted into a halogen and, more particularly, bromine or chlorine, or into a tosylate, mesylate, nosylate or triflate group. More preferably, the conversion into a leaving group is carried out using boron tribromide, thionyl chloride, mesyl chloride, tosyl chloride, trifluoromethanesulphonyl chloride or nosyl chloride. Advantageously, the OH group of the compound of formula (IV) is converted into chlorine by the action of thionyl chloride.

Among the cyanation reagents that may be used in the process of the present invention there may be mentioned, without implying any limitation, trimethylsilyl cyanide, lithium cyanide, sodium cyanide, potassium cyanide and tetrabutylammonium cyanide. The preferred cyanation reagent is potassium cyanide.

The compound of formula (I) thereby obtained is, when required, subjected to reduction and then to a coupling reaction with acetic anhydride to yield agomelatine.

EXAMPLE (7-Methoxy-1-naphthyl)acetonitrile

Step A: (7-Methoxy-1-naphthyl)methanol
To 1 equivalent of 7-methoxy-1-naphthoic acid (100 g) in THF (3.8 ml/g) there are slowly added 2.5 equivalents of 1M $BH_3$-THF (1.235 litres). During the addition, the temperature of the reaction mixture is maintained at 5° C. (+/−2° C.) and then the mixture is left at ambient temperature for 3 hours. After evaporation under reduced pressure, the residue is taken up in dichloromethane and washed with water. The organic phase is dried over $MgSO_4$ and then the solvents are evaporated off under reduced pressure to yield the title compound in the form of a light-brown solid in a yield of 91%.
Melting point: 72-74° C.
Step B: 1-(Chloromethyl)-7-methoxynaphthalene
To a solution of the compound obtained in Step A (100 g) in dichloromethane (5 ml/g) there are added 2 equivalents of thionyl chloride (126.35 g). The mixture is heated to reflux and maintained at reflux for 2 hours. After returning to ambient temperature, the solvent is evaporated off under reduced pressure. The oil obtained is taken up in ethyl acetate and washed with water and then with saturated NaCl solution. The solvent is evaporated off under reduced pressure and the crude product is purified by passing over a pad of silica (eluant: heptane). The title compound is obtained in the form of a yellow solid in a yield of 84%.
Step C: (7-Methoxy-1-naphthyl)acetonitrile
To a solution of the compound obtained in Step B (100 g) in 30 ml/g of DMSO and 5 ml/g of water there are added 1.2 equivalents of potassium cyanide (37.8 g). The reaction mixture is heated to 65° C. and maintained at 65° C. for 3 hours. After returning to ambient temperature, an MTBE/water (1/1) binary system is added to the mixture. The aqueous phase is removed. The organic phase is washed several times with water and then with saturated NaCl solution. The solvents are distilled off and the title compound is obtained in a quantitative yield.
Melting point: 83° C.

The invention claimed is:
1. A process for the synthesis of agomelatine, wherein 7-methoxy-1-naphthoic acid of formula (III):

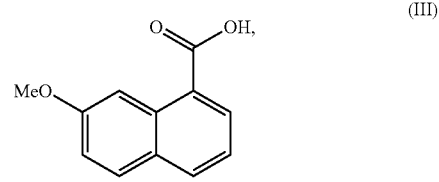 [SMILES: COc1ccc2cccc(C(=O)O)c2c1]

is subjected to the action of a reducing agent to yield a compound of formula (IV):

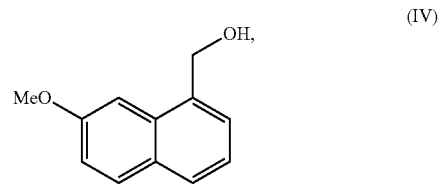 [SMILES: COc1ccc2cccc(CO)c2c1]

the OH function of which compound of formula (IV) is converted into a leaving group and which is reacted with a cyanation reagent to yield a compound of formula (I)

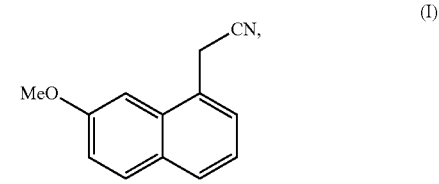 [SMILES: COc1ccc2cccc(CC#N)c2c1]

which is isolated in the form of a solid, wherein the compound of formula (I) so obtained is subjected to reduction and then to coupling with acetic anhydride to yield agomelatine.

2. The process of claim 1, wherein the reduction of the acid of formula (III) is carried out using $BH_3$-THF.

3. The process of claim 1, wherein the OH group of the compound of formula (IV) is converted into chlorine by the action of thionyl chloride.

4. The process of claim 1, wherein the cyanation reagent is potassium cyanide.

* * * * *